United States Patent
Ulrich et al.

(10) Patent No.: US 12,138,425 B2
(45) Date of Patent: Nov. 12, 2024

(54) SYSTEM AND METHOD FOR INCORPORATING EXERCISE INTO CLOSED-LOOP DIABETES THERAPY

(71) Applicant: Tandem Diabetes Care, Inc., San Diego, CA (US)

(72) Inventors: Thomas R. Ulrich, Oceanside, CA (US); Michael Michaud, San Diego, CA (US); Geoffrey A. Kruse, San Diego, CA (US); Paul Harris, San Diego, CA (US); Garrett Marin, San Diego, CA (US)

(73) Assignee: Tandem Diabetes Care, Inc., San Diego, CA (US)

( * ) Notice: Subject to any disclaimer, the term of this patent is extended or adjusted under 35 U.S.C. 154(b) by 569 days.

(21) Appl. No.: 16/879,363

(22) Filed: May 20, 2020

(65) Prior Publication Data
US 2020/0368430 A1    Nov. 26, 2020

Related U.S. Application Data

(60) Provisional application No. 62/850,799, filed on May 21, 2019.

(51) Int. Cl.
*A61M 5/172* (2006.01)
*A61M 5/142* (2006.01)
*G16H 20/17* (2018.01)

(52) U.S. Cl.
CPC .......... *A61M 5/1723* (2013.01); *A61M 5/142* (2013.01); *G16H 20/17* (2018.01);
(Continued)

(58) Field of Classification Search
CPC ....... A61B 5/00; A61M 5/1723; A61M 5/142; A61M 5/14244; A61M 2205/3553;
(Continued)

(56) References Cited

U.S. PATENT DOCUMENTS

| | | |
|---|---|---|
| 5,108,363 A | 4/1992 | Tuttle et al. |
| 5,460,605 A | 10/1995 | Tuttle et al. |

(Continued)

FOREIGN PATENT DOCUMENTS

| | | | | |
|---|---|---|---|---|
| CA | 2930776 C | 5/2018 | | |
| WO | WO-2017184988 A1 * | 10/2017 | ............... | A61B 5/00 |
| WO | WO-2019125932 A1 * | 6/2019 | .......... | A61M 5/1723 |

OTHER PUBLICATIONS

Arthur Bertachi et al.: "Assessment of Mitigation Methods to Reduce the Risk of Hypoglycemia for Announced Exercise in a Uni-hormonal Artificial Pancreas", Diabetes Technology & Therapeutics, vol. 20, No. 4, Apr. 1, 2018, pp. 285-295, XP055731523, Mary Ann Liebert, Larchmont, NY; US ISSN: 1520-9156, DOI: 10.1089/dia.2017.0392, 12 pages.

(Continued)

*Primary Examiner* — Kami A Bosworth
(74) *Attorney, Agent, or Firm* — Merchant & Gould P.C.

(57) ABSTRACT

Disclosed herein are apparatuses and methods that account for exercise in closed loop insulin delivery systems. Rather than increasing a target insulin on board (IOB) as glucose levels rise, which would increase insulin delivery to address the raised glucose levels, when a user indicates that the user will be exercising raised glucose levels are addressed by reducing the target IOB within the closed loop algorithm. By reducing the target IOB, the algorithm responds less aggressively to pre-exercise food, and does not build up the IOB that can cause dangerously low glucose levels once the exercise also begins lowering glucose levels.

19 Claims, 9 Drawing Sheets

(52) U.S. Cl.
CPC .............. *A61M 2005/14208* (2013.01); *A61M 2205/056* (2013.01); *A61M 2205/3553* (2013.01); *A61M 2205/502* (2013.01)

(58) Field of Classification Search
CPC ...... A61M 2205/056; A61M 2205/502; A61M 2005/14208; A61M 5/14248; A61M 2005/14252; A61M 2005/14256; A61M 2005/1426; A61M 2005/14264; A61M 2005/14268; A61M 2005/1726; A61M 2230/201; G16H 20/17; G16H 40/63
See application file for complete search history.

(56) References Cited

U.S. PATENT DOCUMENTS

| | | |
|---|---|---|
| 5,741,211 A | 4/1998 | Renirie et al. |
| 5,822,715 A | 10/1998 | Worthington et al. |
| 6,379,301 B1 | 4/2002 | Worthington et al. |
| 6,572,542 B1 | 6/2003 | Houben et al. |
| 6,692,456 B1 | 2/2004 | Eppstein et al. |
| 7,404,796 B2 | 7/2008 | Ginsberg |
| 7,497,827 B2 | 3/2009 | Brister et al. |
| 7,515,060 B2 | 4/2009 | Blomquist |
| 7,621,893 B2 | 11/2009 | Moberg et al. |
| 7,711,402 B2 | 5/2010 | Shults et al. |
| 7,766,873 B2 | 8/2010 | Moberg et al. |
| 7,998,111 B2 | 8/2011 | Moberg et al. |
| 8,062,257 B2 | 11/2011 | Moberg et al. |
| 8,065,096 B2 | 11/2011 | Moberg et al. |
| RE43,316 E | 4/2012 | Brown et al. |
| 8,182,447 B2 | 5/2012 | Moberg et al. |
| 8,257,300 B2 | 9/2012 | Budiman et al. |
| 8,267,893 B2 | 9/2012 | Moberg et al. |
| 8,287,487 B2 | 10/2012 | Estes |
| 8,287,495 B2 | 10/2012 | Michaud et al. |
| 8,311,749 B2 | 11/2012 | Brauker et al. |
| 8,369,919 B2 | 2/2013 | Kamath et al. |
| 8,377,031 B2 | 2/2013 | Hayter et al. |
| 8,573,027 B2 | 11/2013 | Rosinko et al. |
| 8,712,748 B2 | 4/2014 | Thukral |
| 8,818,782 B2 | 8/2014 | Thukral |
| 8,986,253 B2 | 3/2015 | DiPerna |
| 9,114,210 B2 | 8/2015 | Estes |
| 9,381,297 B2 | 7/2016 | Brown et al. |
| 9,486,171 B2 | 11/2016 | Saint |
| 9,669,160 B2 | 6/2017 | Harris |
| 9,833,177 B2 | 12/2017 | Blomquist |
| 9,844,627 B2 | 12/2017 | Estes |
| 9,867,937 B2 | 1/2018 | Saint et al. |
| 9,867,953 B2 | 1/2018 | Rosinko |
| 10,016,561 B2 | 7/2018 | Saint et al. |
| 10,052,049 B2 | 8/2018 | Blomquist et al. |
| 10,213,547 B2 | 2/2019 | Rosinko |
| 10,279,106 B1 | 5/2019 | Cook et al. |
| 10,357,606 B2 | 7/2019 | Rosinko et al. |
| 10,357,607 B2 | 7/2019 | Blomquist et al. |
| 10,549,051 B2 | 2/2020 | Rosinko |
| 10,569,016 B2 | 2/2020 | Rosinko |
| 10,864,322 B2 | 12/2020 | Saint et al. |
| 2003/0225360 A1 | 12/2003 | Eppstein |
| 2005/0049179 A1 | 3/2005 | Davidson |
| 2007/0083335 A1 | 4/2007 | Moerman |
| 2008/0106431 A1 | 5/2008 | Blomquist |
| 2008/0171967 A1 | 7/2008 | Blomquist et al. |
| 2008/0172026 A1 | 7/2008 | Blomquist |
| 2008/0172027 A1 | 7/2008 | Blomquist |
| 2008/0172028 A1 | 7/2008 | Blomquist |
| 2008/0172029 A1 | 7/2008 | Blomquist |
| 2008/0172030 A1 | 7/2008 | Blomquist |
| 2008/0172031 A1 | 7/2008 | Blomquist |
| 2008/0183060 A1 | 7/2008 | Steil et al. |
| 2008/0221523 A1 | 9/2008 | Moberg et al. |
| 2008/0228056 A1 | 9/2008 | Blomquist et al. |
| 2008/0275384 A1* | 11/2008 | Mastrototaro ....... A61B 5/6849 604/65 |
| 2009/0006061 A1 | 1/2009 | Thukral |
| 2009/0006129 A1 | 1/2009 | Thukral |
| 2009/0105636 A1 | 4/2009 | Hayter |
| 2009/0192366 A1 | 7/2009 | Mensinger et al. |
| 2009/0192745 A1 | 7/2009 | Kamath et al. |
| 2010/0037680 A1 | 2/2010 | Moberg et al. |
| 2010/0094251 A1 | 4/2010 | Estes |
| 2010/0121170 A1 | 5/2010 | Rule |
| 2010/0174266 A1 | 7/2010 | Estes |
| 2010/0217192 A1 | 8/2010 | Moberg et al. |
| 2010/0217193 A1 | 8/2010 | Moberg et al. |
| 2011/0046051 A1 | 2/2011 | Moerman |
| 2011/0046892 A1 | 2/2011 | Moerman |
| 2011/0054391 A1 | 3/2011 | Ward et al. |
| 2012/0330227 A1 | 12/2012 | Budiman et al. |
| 2013/0053816 A1 | 2/2013 | DiPerna et al. |
| 2013/0324928 A1 | 12/2013 | Kruse et al. |
| 2014/0012511 A1 | 1/2014 | Mensinger et al. |
| 2014/0180203 A1 | 6/2014 | Budiman |
| 2014/0276419 A1 | 9/2014 | Rosinko et al. |
| 2015/0120317 A1* | 4/2015 | Mayou .................. G16H 40/63 705/2 |
| 2015/0217052 A1 | 8/2015 | Keenan et al. |
| 2016/0199571 A1 | 7/2016 | Rosinko et al. |
| 2016/0339172 A1 | 11/2016 | Michaud et al. |
| 2017/0000943 A1 | 1/2017 | Blomquist et al. |
| 2017/0049957 A1 | 2/2017 | Michaud |
| 2017/0189614 A1* | 7/2017 | Mazlish ............. A61M 5/1452 |
| 2017/0220751 A1* | 8/2017 | Davis .................. A61B 5/7264 |
| 2018/0092578 A1 | 4/2018 | Blomquist |
| 2018/0093039 A1 | 4/2018 | Estes |
| 2018/0133397 A1 | 5/2018 | Estes |
| 2019/0328967 A1 | 10/2019 | Blomquist et al. |
| 2019/0350501 A1 | 11/2019 | Blomquist et al. |
| 2019/0365997 A1 | 12/2019 | Harris |
| 2019/0388015 A1 | 12/2019 | Blomquist |
| 2020/0101226 A1 | 4/2020 | Rosinko et al. |
| 2020/0114076 A1 | 4/2020 | Ulrich et al. |
| 2020/0171249 A1 | 6/2020 | Rosinko |
| 2020/0179603 A1 | 6/2020 | Rosinko |
| 2020/0254174 A1 | 8/2020 | Kruse et al. |
| 2020/0261649 A1 | 8/2020 | Michaud et al. |
| 2021/0001044 A1 | 1/2021 | Michaud et al. |

OTHER PUBLICATIONS

Arthur Bertachi et al.: Exercise-induced hypoglycemia in type 1 diabetes: in-silico comparison between announced and unannounced strategies in closed-loop control, IFAC-Papersonline, vol. 52, No. 1, Apr. 26, 2019, pp. 1000-1005, XP055731519, DE ISSN: 2405-8963, DOI: 10.1016/j.ifacol.2019.06.193, 6 pages.
Michael C. Riddell et al.: "Exercise management in type 1 diabetes: a consensus statement", May 1, 2017, XP055732151, Retrived from the Internet: URL:https://www.digibete.org/wp-content/uploads/2018/01/Exercise-management-in-type-1-diabetes-a-consenses-Mike-Riddell-Lancet-DE-2017.pdf [Retrieved on Sep. 18, 2020], 14 pages.
Search Report dated Sep. 29, 2020 for EP Application No. 20175932. 1, 11 pages.

* cited by examiner

SYSTEM AND METHOD FOR INCORPORATING EXERCISE INTO CLOSED-LOOP DIABETES THERAPY

RELATED APPLICATION

The present application claims the benefit of U.S. Provisional Application No. 62/850,799 filed May 21, 2019, which is hereby incorporated herein in its entirety by reference.

FIELD OF THE INVENTION

The present invention relates generally to ambulatory infusion pumps and, more particularly, to operation of ambulatory infusion pumps in a closed-loop or semi-closed-loop fashion.

BACKGROUND OF THE INVENTION

There are a wide variety of medical treatments that include the administration of a therapeutic fluid in precise, known amounts at predetermined intervals. Devices and methods exist that are directed to the delivery of such fluids, which may be liquids or gases, are known in the art.

One category of such fluid delivery devices includes insulin injecting pumps developed for administering insulin to patients afflicted with type I, or in some cases, type II diabetes. Some insulin injecting pumps are configured as portable or ambulatory infusion devices can provide continuous subcutaneous insulin injection and/or infusion therapy as an alternative to multiple daily injections of insulin via a syringe or an insulin pen. Such pumps are worn by the user and may use replaceable cartridges. In some embodiments, these pumps may also deliver medicaments other than, or in addition to, insulin, such as glucagon, pramlintide, and the like. Examples of such pumps and various features associated therewith include those disclosed in U.S. Patent Publication Nos. 2013/0324928 and 2013/0053816 and U.S. Pat. Nos. 8,287,495; 8,573,027; 8,986,253; and 9,381,297, each of which is incorporated herein by reference in its entirety.

Ambulatory infusion pumps for delivering insulin or other medicaments can be used in conjunction with blood glucose monitoring systems, such as blood glucose meters (BGMs) and continuous glucose monitoring devices (CGMs). A CGM provides a substantially continuous estimated blood glucose level through a transcutaneous sensor that estimates blood analyte levels, such as blood glucose levels, via the patient's interstitial fluid. CGM systems typically consist of a transcutaneously-placed sensor, a transmitter and a monitor.

Ambulatory infusion pumps typically allow the patient or caregiver to adjust the amount of insulin or other medicament delivered, by a basal rate or a bolus, based on blood glucose data obtained by a BGM or a CGM, and in some cases include the capability to automatically adjust such medicament delivery. Some ambulatory infusion pumps may include the capability to interface with a BGM or CGM such as, e.g., by receiving measured or estimated blood glucose levels and automatically adjusting or prompting the user to adjust the level of medicament being administered or planned for administration or, in cases of abnormally low blood glucose readings, reducing or automatically temporarily ceasing or prompting the user temporarily to cease or reduce insulin administration. These portable pumps may incorporate a BGM or CGM within the hardware of the pump or may communicate with a dedicated BGM or CGM via wired or wireless data communication protocols, directly and/or via a device such as a smartphone. One example of integration of infusion pumps with CGM devices is described in U.S. Patent Publication No. 2014/0276419, which is hereby incorporated by reference herein.

As noted above, insulin or other medicament dosing by basal rate and/or bolus techniques could automatically be provided by a pump based on readings received into the pump from a CGM device that is, e.g., external to the portable insulin pump or integrated with the pump as a pump-CGM system in a closed-loop or semi-closed-loop fashion. With respect to insulin delivery, some systems including this feature can be referred to as artificial pancreas systems because the systems serve to mimic biological functions of the pancreas for patients with diabetes.

Exercise is known to affect glucose levels in unpredictable ways and can cause challenges for accurate closed-loop or semi-closed loop treatment of diabetes even with use of a CGM. The body's response to exercise varies depending upon a number of factors, including intensity of exercise. For example, aerobic exercise tends to lower blood glucose while anaerobic exercise tends to increase blood glucose. With closed-loop therapy, the control algorithm will generally increase the delivery of insulin upon detecting a rise in glucose level after the user eats. If a user then begins to exercise aerobically after eating, the exercise plus the increase in insulin can cause a severe drop in blood glucose. The variability of the body's response to exercise makes accounting for such circumstances with closed loop therapy challenging

SUMMARY

Disclosed herein are apparatuses and methods that account for exercise in closed loop insulin delivery systems. Rather than increasing a target insulin on board (IOB) as glucose levels rise, which would increase insulin delivery to address the raised glucose levels, the apparatuses and methods disclosed herein address exercise-induced glucose level increases by reducing the target IOB within the closed loop. By reducing the target IOB, the algorithm responds less aggressively to pre-exercise food, and does not build up the IOB that could potentially contribute to undesirably low glucose levels once the exercise also begins lowering glucose levels.

In an embodiment, a system for closed loop diabetes therapy includes a pump mechanism configured to facilitate delivery of insulin to a user, a user interface, a communications device adapted to receive glucose levels from a CGM and a processor functionally linked to the pump mechanism, the user interface and the communications device. The processor can be configured to calculate and deliver insulin doses to the user based on a closed loop insulin delivery algorithm. The closed loop insulin delivery algorithm can include an outer glucose loop that compares glucose levels from the CGM to a glucose target to determine an IOB target for the user and an inner IOB loop that compares an estimated IOB for the user to the IOB target to determine an IOB error used to calculate insulin doses configured to maintain the IOB of the user at the IOB target and the glucose levels of the user at the glucose level target. If the processor receives an indication that the user will be exercising, the processor can activate an exercise mode for the closed loop insulin delivery algorithm that modifies the inner IOB loop of the closed loop delivery algorithm that calculates insulin doses to maintain the IOB of the user at the IOB target. The processor can then calculate and deliver insulin doses to the user based on glucose levels from the CGM according to the exercise mode of the closed loop insulin delivery algorithm following the indication that the user will be exercising.

In an embodiment, a method of closed loop diabetes therapy includes receiving glucose levels of a user from a CGM and calculating insulin doses to the user based on a closed loop insulin delivery algorithm. The closed loop insulin delivery algorithm can include an outer glucose loop that compares glucose levels from the CGM to a glucose target to determine an IOB target for the user and an inner IOB loop that compares an estimated IOB for the user to the IOB target to determine an IOB error used to calculate insulin doses configured to maintain the IOB of the user at the IOB target and the glucose levels of the user at the glucose level target. The calculated insulin doses can be delivered to the user with a pump mechanism. If an indication that the user will be exercising is received, an exercise mode for the closed loop insulin delivery algorithm can be activated. The exercise mode can modify the inner IOB loop of the closed loop delivery algorithm that calculates insulin doses to maintain the IOB of the user at the IOB target. Insulin doses can then be calculated and delivered to the user based on glucose levels from the CGM according to the exercise mode of the closed loop insulin delivery algorithm following the indication that the user will be exercising.

BRIEF DESCRIPTION OF THE DRAWINGS

The invention may be more completely understood in consideration of the following detailed description of various embodiments of the invention in connection with the accompanying drawings, in which.

While the invention is amenable to various modifications and alternative forms, specifics thereof have been shown by way of example in the drawings and will be described in detail. It should be understood, however, that the intention is not to limit the invention to the particular embodiments described. On the contrary, the intention is to cover all modifications, equivalents, and alternatives falling within the spirit and scope of the invention.

DETAILED DESCRIPTION OF THE INVENTION

The following detailed description should be read with reference to the drawings in which similar elements in different drawings are numbered the same. The drawings, which are not necessarily to scale, depict illustrative embodiments and are not intended to limit the scope of the invention.

Figure 1:
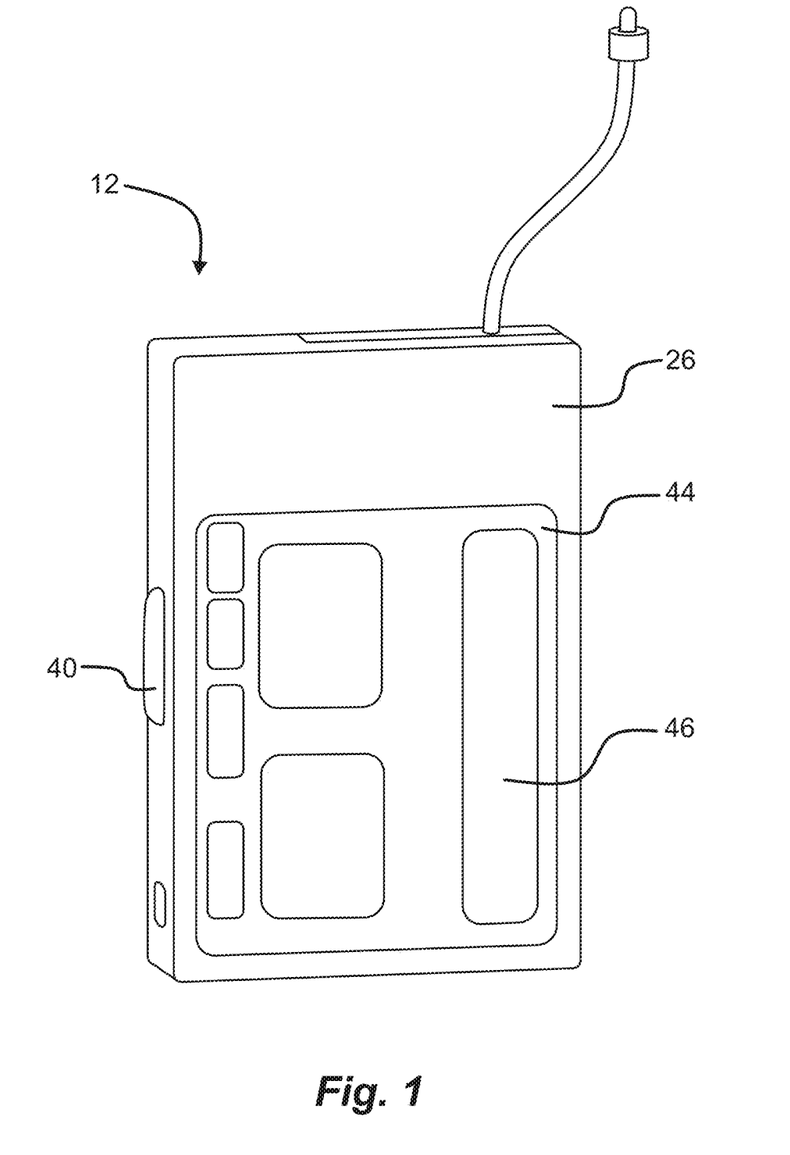
FIG. 1 is a medical device that can be used with embodiments of the disclosure.

FIG. 1 depicts an embodiment of a medical device according to the disclosure. In this embodiment, the medical device is configured as a pump 12, such as an infusion pump, that can include a pumping or delivery mechanism and reservoir for delivering medicament to a patient and an output/display 44. The output/display 44 may include an interactive and/or touch sensitive screen 46 having an input device such as, for example, a touch screen comprising a capacitive screen or a resistive screen. The pump 12 may additionally or instead include one or more of a keyboard, a microphone or other input devices known in the art for data entry, some or all of which may be separate from the display. The pump 12 may also include a capability to operatively couple to one or more other display devices such as a remote display, a remote control device, a laptop computer, personal computer, tablet computer, a mobile communication device such as a smartphone, a wearable electronic watch or electronic health or fitness monitor, or personal digital assistant (PDA), a CGM display etc.

In one embodiment, the medical device can be an ambulatory insulin pump configured to deliver insulin to a patient. Further details regarding such pump devices can be found in U.S. Pat. No. 8,287,495, which is incorporated herein by reference in its entirety. In other embodiments, the medical device can be an infusion pump configured to deliver one or more additional or other medicaments to a patient.

Figure 2:
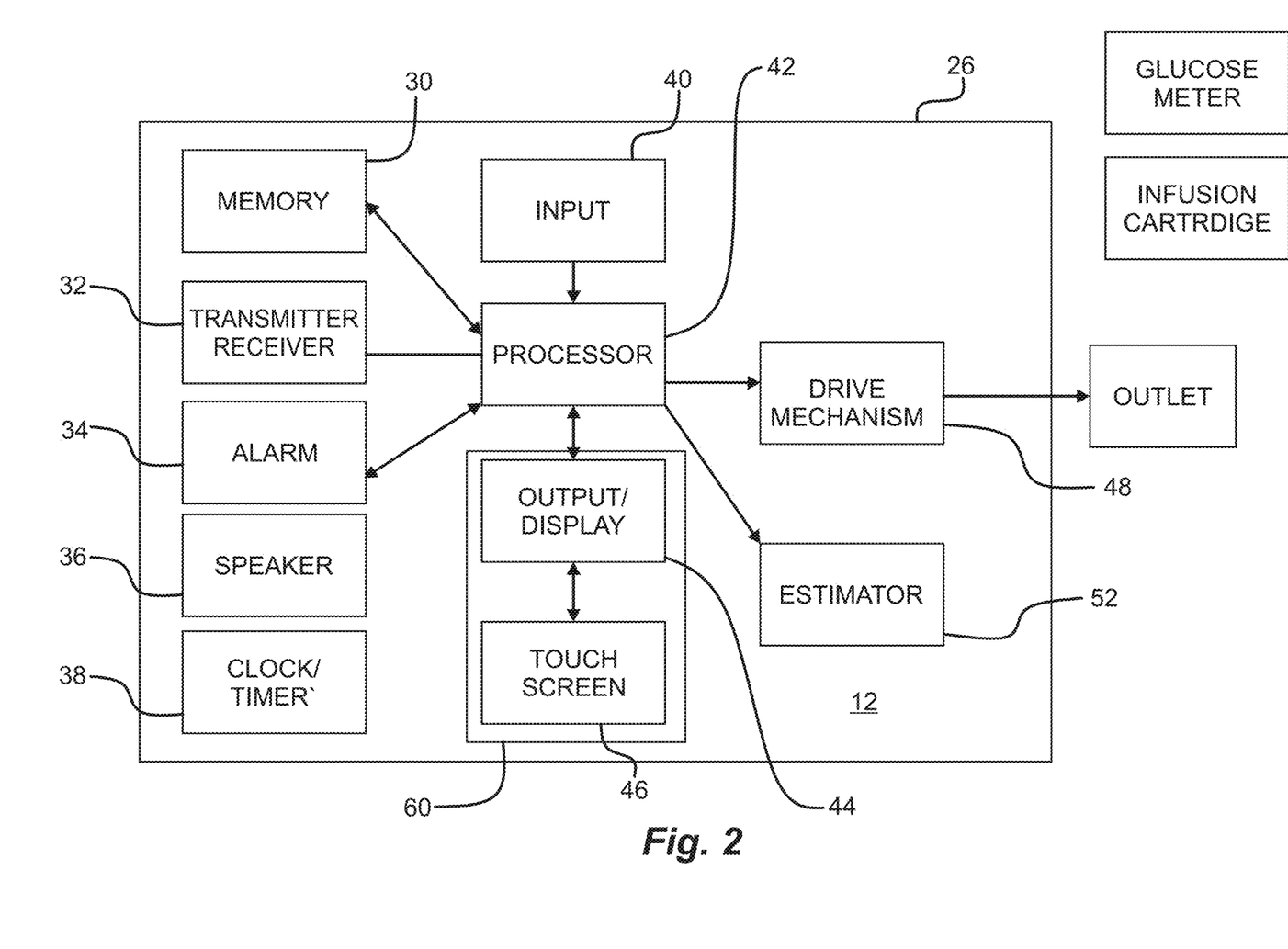
FIG. 2 is a block diagram representing a medical device that can be used with embodiments of the disclosure.

FIG. 2 illustrates a block diagram of some of the features that can be used with embodiments, including features that may be incorporated within the housing 26 of a medical device such as a pump 12. The pump 12 can include a processor 42 that controls the overall functions of the device. The infusion pump 12 may also include, e.g., a memory device 30, a transmitter/receiver 32, an alarm 34, a speaker 36, a clock/timer 38, an input device 40, a user interface suitable for accepting input and commands from a user such as a caregiver or patient, a drive mechanism 48, an estimator device 52 and a microphone (not pictured). One embodiment of a user interface is a graphical user interface (GUI) 60 having a touch sensitive screen 46 with input capability. In some embodiments, the processor 42 may communicate with one or more other processors within the pump 12 and/or one or more processors of other devices, for example, a continuous glucose monitor (CGM), display device, smartphone, etc. through the transmitter/receiver. The processor 42 may also include programming that may allow the processor to receive signals and/or other data from an input device, such as a sensor that may sense pressure, temperature or other parameters.

Figures 3A, 3B:
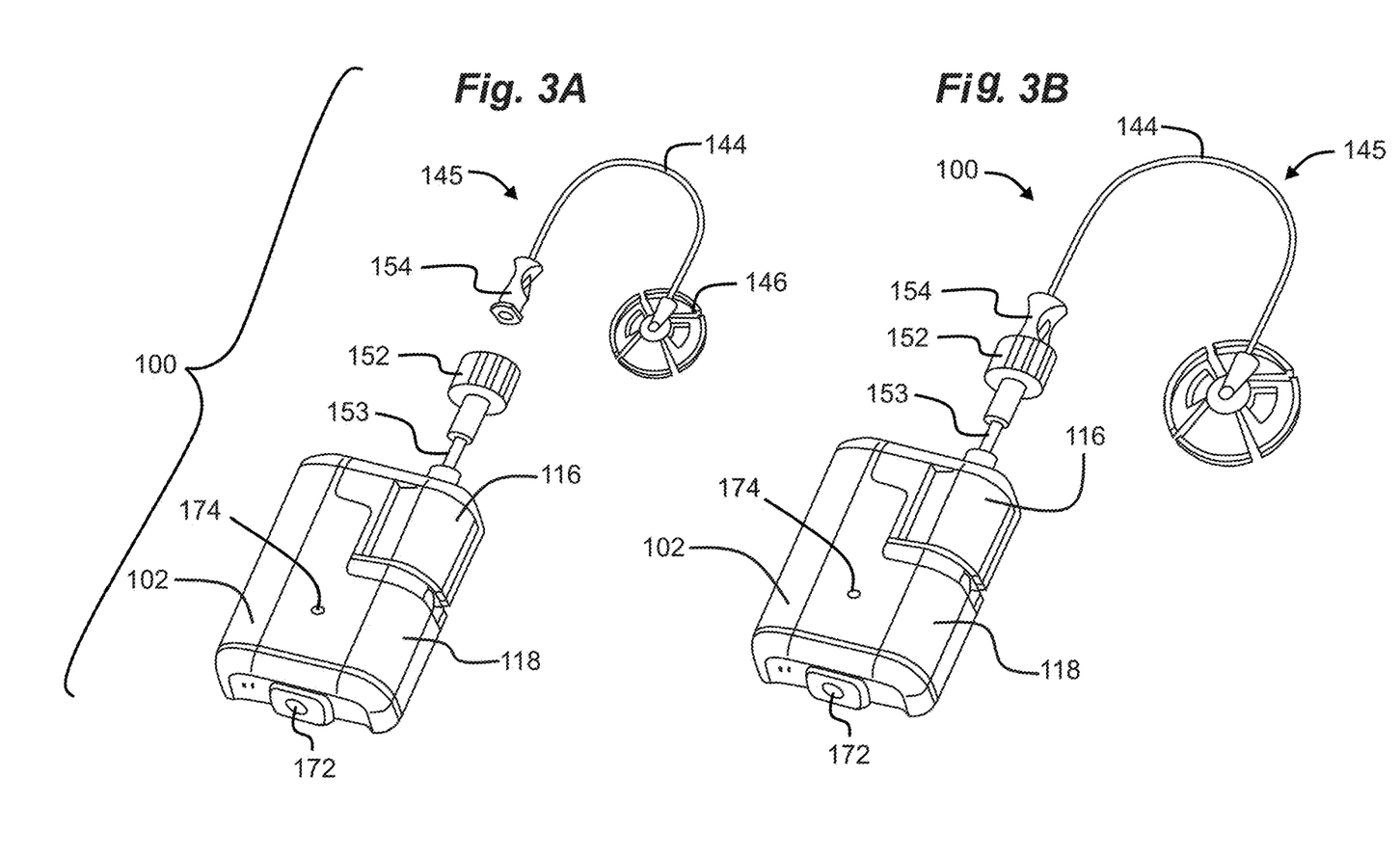
FIGS. 3A-3B depict an embodiment of a pump system according to the disclosure.

FIGS. 3A-3B depict another pump system including a pump 102 that can be used with embodiments. Drive unit 118 of pump 102 includes a drive mechanism 122 that mates with a recess in disposable cartridge 116 of pump 102 to attach the cartridge 116 to the drive unit 118. Pump system 100 can further include an infusion set 145 having a connector 154 that connects to a connector 152 attached to pump 102 with tubing 153. Tubing 144 extends to a site connector 146 that can attach or be pre-connected to a cannula and/or infusion needle that punctures the patient's skin at the infusion site to deliver medicament from the pump 102 to the patient via infusion set 145. In some embodiments, pump can include a user input button 172 and an indicator light 174 to provide feedback to the user.

In one embodiment, pump 102 includes a processor that controls operations of the pump and, in some embodiments, may receive commands from a separate device for control of operations of the pump. Such a separate device can include, for example, a dedicated remote control or a smartphone or other consumer electronic device executing an application configured to enable the device to transmit operating commands to the processor of pump 102. In some embodiments, processor can also transmit information to one or more separate devices, such as information pertaining to device parameters, alarms, reminders, pump status, etc. In one embodiment pump 102 does not include a display but may include one or more indicator lights 174 and/or one or more input buttons 172. Pump 102 can also incorporate any or all of the features described with respect to pump 12 in FIG. 2. Further details regarding such pumps can be found in U.S. Pat. No. 10,279,106 and U.S. Patent Publication Nos. 2016/0339172 and 2017/0049957, each of which is hereby incorporated herein by reference in its entirety.

Figure 4:
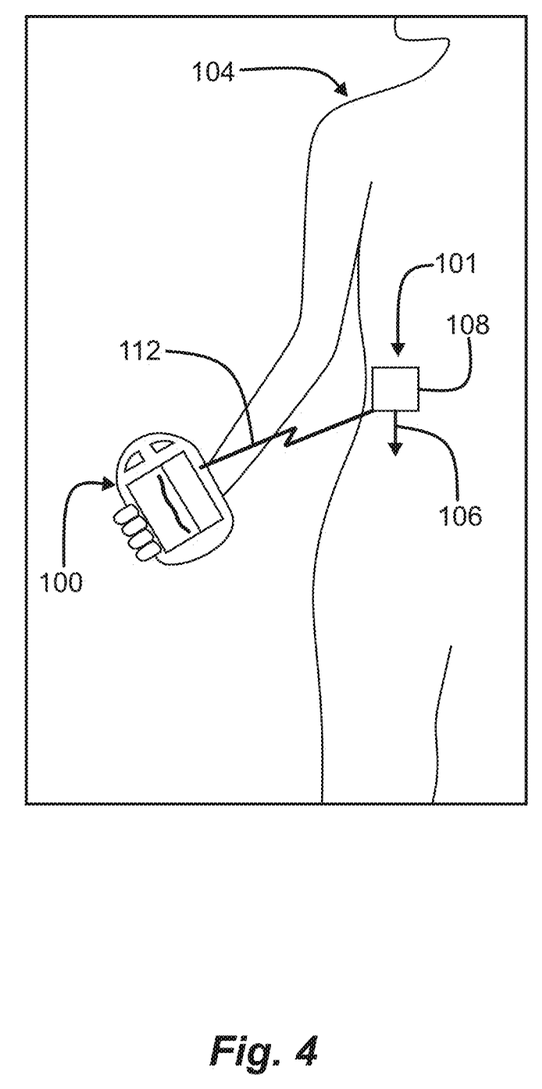
FIG. 4 is a schematic representation of a system according to the disclosure.

Pump 12 or 102 can interface directly or indirectly (via, e.g., a smartphone or other device) with a glucose meter, such as a blood glucose meter (BGM) or a continuous glucose monitor (CGM). Referring to FIG. 4, an exemplary CGM system 100 according to an embodiment of the present invention is shown (other CGM systems can be used). The illustrated CGM system includes a sensor 101 affixed to a patient 104 that can be associated with the insulin infusion device in a CGM-pump system. The sensor 101 includes a sensor probe 106 configured to be inserted to a point below the dermal layer (skin) of the patient 104. The sensor probe 106 is therefore exposed to the patient's interstitial fluid or plasma beneath the skin and reacts with that interstitial fluid to produce a signal that can be associated with the patient's blood glucose (BG) level. The sensor 101 includes a sensor body 108 that transmits data associated with the interstitial fluid to which the sensor probe 106 is exposed. The data may be transmitted from the sensor 101 to the glucose monitoring system receiver 100 via a wireless transmitter, such as a near field communication (NFC) radio frequency (RF) transmitter or a transmitter operating according to a "Wi-Fi" or Bluetooth® protocol, Bluetooth® low energy protocol or the like, or the data may be transmitted via a wire connector from the sensor 101 to the monitoring system 100. Transmission of sensor data to the glucose monitoring system receiver by wireless or wired connection is represented in FIG. 4 by the arrow line 112. Further detail regarding such systems and definitions of related terms can be found in, e.g., U.S. Pat. Nos. 8,311,749, 7,711,402 and 7,497,827, each of which is hereby incorporated by reference in its entirety.

In an embodiment of a pump-CGM system having a pump 12, 102 that communicates with a CGM and that integrates CGM data and pump data as described herein, the CGM can automatically transmit the glucose data to the pump. The pump can then automatically determine therapy parameters and deliver medicament based on the data. Such an automatic pump-CGM system for insulin delivery can be referred to as an automated insulin delivery (AID) or an artificial pancreas system that provides closed-loop therapy to the patient to approximate or even mimic the natural functions of a healthy pancreas. In such a system, insulin doses are calculated based on the CGM readings (that may or may not be automatically transmitted to the pump) and are automatically delivered to the patient at least in part based on the CGM reading(s). In various embodiments, doses can be delivered as automated correction boluses and/or automated increases or decreases to a basal rate. Insulin doses can also be administered based on current glucose levels and/or predicted future glucoses levels based on current and past glucose levels.

For example, if the CGM indicates that the user has a high blood glucose level or hyperglycemia, the system can automatically calculate an insulin dose necessary to reduce the user's blood glucose level below a threshold level or to a target level and automatically deliver the dose. Alternatively, the system can automatically suggest a change in therapy upon receiving the CGM data such as an increased insulin basal rate or delivery of a bolus, but can require the user to accept the suggested change prior to delivery rather than automatically delivering the therapy adjustments.

If the CGM data indicates that the user has a low blood glucose level or hypoglycemia, the system can, for example, automatically reduce a basal rate, suggest to the user to reduce a basal rate, automatically deliver or suggest that the user initiate the delivery of an amount of a substance such as, e.g., a hormone (glucagon) to raise the concentration of glucose in the blood, automatically suggest that the user, e.g., ingest carbohydrates and/or take other actions and/or make other suggestions as may be appropriate to address the hypoglycemic condition, singly or in any desired combination or sequence. Such determination can be made by the infusion pump providing therapy or by a separate device that transmits therapy parameters to the infusion pump. In some embodiments, multiple medicaments can be employed in such a system as, for example, a first medicament, e.g., insulin, that lowers blood glucose levels and a second medicament, e.g., glucagon, that raises blood glucose levels.

As with other parameters related to therapy, such thresholds and target values can be stored in memory located in the pump or, if not located in the pump, stored in a separate location and accessible by the pump processor (e.g., "cloud" storage, a smartphone, a CGM, a dedicated controller, a computer, etc., any of which is accessible via a network connection). The pump processor can periodically and/or continually execute instructions for a checking function that accesses these data in memory, compares them with data received from the CGM and acts accordingly to adjust therapy. In further embodiments, rather than the pump determining the therapy parameters, the parameters can be determined by a separate device and transmitted to the pump for execution. In such embodiments, a separate device such as the CGM or a device in communication with the CGM, such as, for example, a smartphone, dedicated controller, electronic tablet, computer, etc. can include a processor programmed to calculate therapy parameters based on the CGM data that then instruct the pump to provide therapy according to the calculated parameters.

Figure 5:
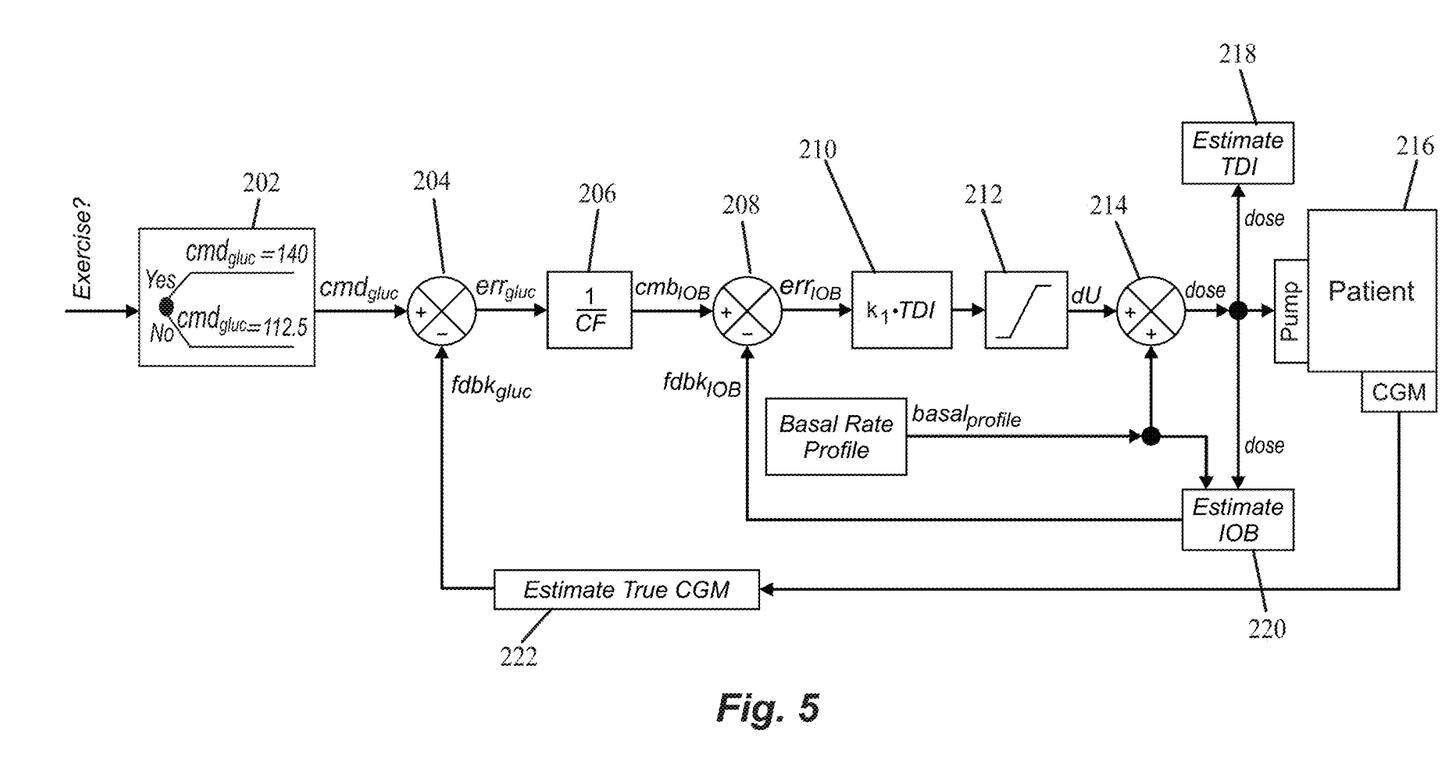
FIG. 5 is a schematic representation of a closed-loop insulin delivery algorithm according to the disclosure.

A schematic representation of a control algorithm for automatically adjusting insulin delivery based on CGM data is depicted in FIG. 5. This figure depicts an algorithm for increasing basal rate that utilizes a cascaded loop. The logic for decreasing basal rate is not depicted. In the depicted embodiment, there is a glucose set-point/command (cmd) that is determined at step 202. The glucose set point is a target value at which the algorithm attempts to maintain a user's blood glucose. This value can vary based on a number of factors, including the user's physiology, whether the user is awake or asleep, how long the user has been awake, etc. In one embodiment, the glucose set point is 140 mg/dL if the user is exercising and 112.5 mg/dL if the user is not exercising. The glucose set point is compared to the actual CGM feedback (fdbk) at step 204 to determine a glucose error value (err) that is the difference between the set point and the feedback. The errGLUCOSE value at step 206 is multiplied by a constant (1/CF), in which CF is the user's correction factor, or amount by which one unit of insulin lowers the user's blood glucose. This calculation determines how much insulin is needed to correct the glucose error, which is how much insulin on board (IOB) is needed in the user's body. This IOB value then determines an appropriate estimated insulin on board (IOB) set point for the patient.

The estimated IOB level determined at step 206 is then taken as the command (cmdIOB) for the inner loop and based on a difference of an IOB feedback value (fdbkIOB) and the cmdIOB set point at step 208, an IOB error value (errIOB) is determined. At step 210, the errIOB value is multiplied by a constant k2 (relating to insulin-dependent glucose uptake in the body) and an estimate of the total daily insulin (TDI) of the user. This adjusts the errIOB to be proportional to the constant and the user's total daily intake of insulin. At step 212, a limiter function is applied to the value calculated at step 210. The limiter function prevents the calculated amount from being larger or smaller than preset limits. The result is an insulin amount dU, which is the amount by which the user's stored basal rate should be modified. The insulin delivery rate for the user for the next closed loop interval is therefore calculated by modifying the user's stored basal rate profile by the dU value at step 214.

After the dose is calculated, it can be delivered to the user at step 216 and can also be used to update the estimated TDI for the user at step 218. The dose can also be used to update the estimated IOB level for the user at step 220 by comparing the actual insulin delivered to the programmed basal rate. The updated estimated IOB then becomes the new fdbkIOB for the IOB comparison at step 208. When new CGM values are received from the CGM, an estimated true CGM can be determined based on various factors such as, for example, the calibration status of the CGM sensor, and the estimated true CGM value then becomes the new fdbkGLUCOSE value for the outer loop comparison with cmdGLUCOSE at step 204. The algorithm then proceeds through to calculate a new estimated IOB and to the inner IOB loop for calculation of an insulin dose as described above. In one embodiment, a new CGM value is received every 5 minutes and therefore the algorithm executes as set forth above every 5 minutes.

Applicant has determined that the difficulties in accounting for exercise in such closed loop controls are caused by the estimated IOB. For example, when the user consumes food the algorithm increases the estimated IOB in response to the increase in insulin delivered to address rising blood glucose, and that increased estimated IOB can cause blood glucose to go low during exercise. For example, for an individual with a total daily insulin (TDI) of 50 units, the algorithm of FIG. 5 would generally respond to a very high glucose level (e.g., 250 mg/dL) by increasing insulin delivery to maintain an IOB of three units. The goal of maintaining this IOB target is ultimately the problem when exercise is involved. In embodiments, the present disclosure addresses this issue by modifying the IOB algorithm instead of raising the glucose target. During exercise, the algorithm can be altered to reduce this IOB target. For example, in the above example for the individual with a TDI of 50 units, the IOB target can be reduced, such as, for example, by 50%. The IOB target can be reduced on either a linear or non-linear schedule based on the intensity of the exercise. For example, for intense exercise such as running a marathon the IOB target could be reduced by 80% whereas for more casual exercise such as a hike along the coast, the target could be reduced by 20%.

In some embodiments, a user will indicate to the system that the user will be exercising, such as, for example, by selecting to enter an exercise mode through a user interface of a pump, remote control, etc. In other embodiments, the system can automatically determine that the user is exercising. In some embodiments, the system can make this determination based on information from one or more additional devices, such as, for example, a fitness or health monitoring device or application. The system may remain in exercise mode for a predetermined time that can be determined in various ways. For example, a user may enter or select an amount of time that the user will exercise or starting time and an ending time for exercise. The user may also be able to disable or close the exercise mode following the exercise through a user interface of a pump, remote control etc. In embodiments that automatically determine when the user is exercising based on information from one or more additional devices, the system can automatically determine when the user has stopped exercising based on the information from the one or more additional devices.

Figure 6:
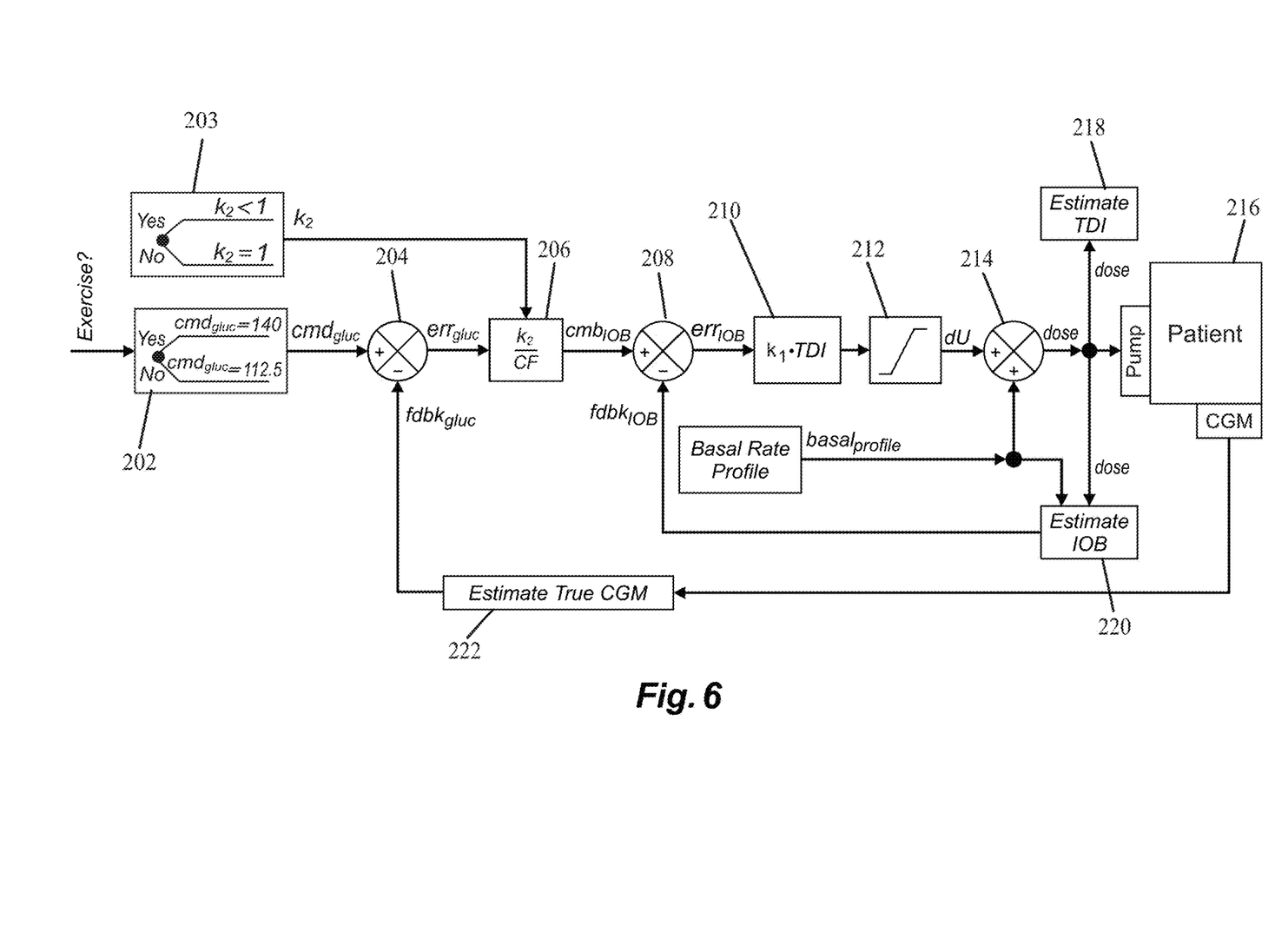
FIG. 6 is a schematic representation of a closed-loop insulin delivery algorithm according to the disclosure.

FIG. 6 depicts a first potential modification to the algorithm of FIG. 5 to account for exercise that involves the IOB set-point. When in exercise mode, a constant $k_2$, which can be a fraction between 0 and 1, is determined at step 203 and multiplied by the IOB set-point determined using the correction factor (CF) in step 206 in place of the 1/CF factor utilized in FIG. 5. In embodiments, this constant will be used to account for the exercise such that the glucose set point is not adjusted at step 202 and that step is bypassed. In other embodiments, the constant can be applied in addition to the glucose set point being adjusted at step 202. By reducing the target IOB with the constant, the errIOB value determined by the comparison with the IOB feedback at step 208 is reduced. The algorithm therefore responds less aggressively to pre-exercise food and does not build up the estimated IOB that can eventually cause the dangerously low blood glucose level during subsequent exercise. Referring to FIG. 6, when in exercise mode the algorithm deviates from the initial glucose level comparison and instead sets the $k_2$ constant at a value less than 1 and then proceeds to calculate the IOB set-point and insulin dose with the remainder of the algorithm as set forth above.

Figure 7:
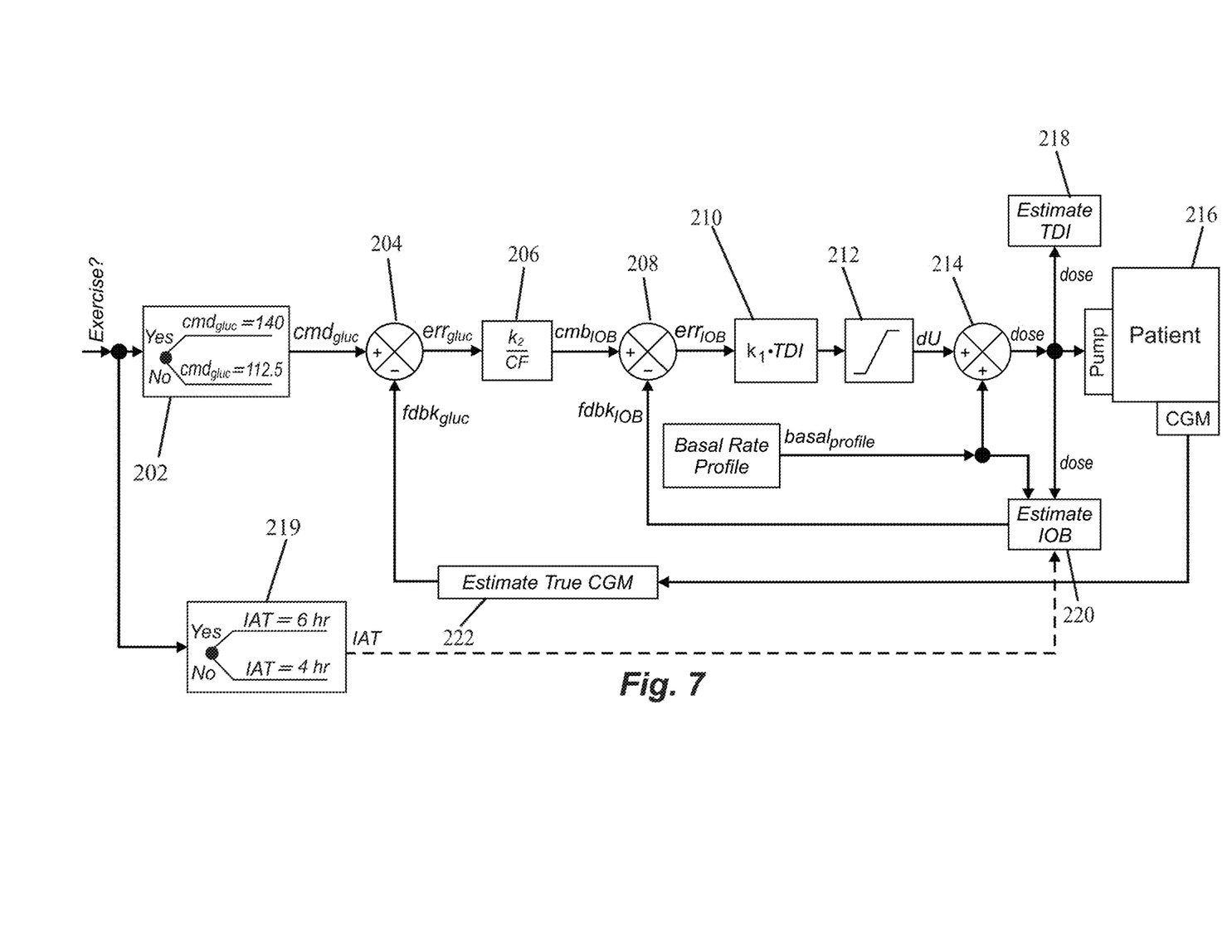
FIG. 7 is a schematic representation of a closed-loop insulin delivery algorithm according to the disclosure.

A second potential modification to the algorithm of FIG. 5 is depicted in FIG. 7. This modification involves using a longer insulation duration time. The initial glucose set point may or not be adjusted for exercise in step 202. As depicted in the bottom left portion of FIG. 7, the algorithm initially bypasses the glucose level comparison when in exercise mode to instead modify the insulin duration time at step 219 for the estimated IOB calculation at step 220. In embodiments, the algorithm typically assumes an insulin action time of four hours. By switching to a longer insulin action time, such as, for example, six hours, previous insulin deliveries are included in the estimated insulin on board determination at step 220 for a longer time, which increases the IOB feedback value and decreases the errorIOB value calculated at IOB comparison step 208 and used in calculating the insulin dose. The action of the control law is therefore reduced, which results in more conservative automatic boluses and basal increases because the algorithm will remember and consider active previous insulin deliveries for a longer time. The algorithm then executes as set forth above to calculate an insulin dose at step 214, but using the modified insulin action time that results in a reduced errIOB value. In ultimately reducing the errIOB value, this embodiment essentially functions similarly to the previous embodiment employing the constant $k_2$, but does so in a different manner by modifying a different portion of the closed loop algorithm.

It should further be noted that be increasing the estimated IOB the above embodiments provide a further safeguard against a manual bolus administered during exercise mode causing an unsafe drop in glucose. Manual boluses during closed loop mode take into account the estimated IOB in the system and only dose as needed to increase the current estimated IOB to match the amount requested in the bolus. Therefore, by increasing the estimated IOB the amount of insulin delivered in any given bolus request is necessarily reduced, which decreases the risk of the bolus in conjunction with exercise causing a dangerously low level of glucose.

Figure 8:
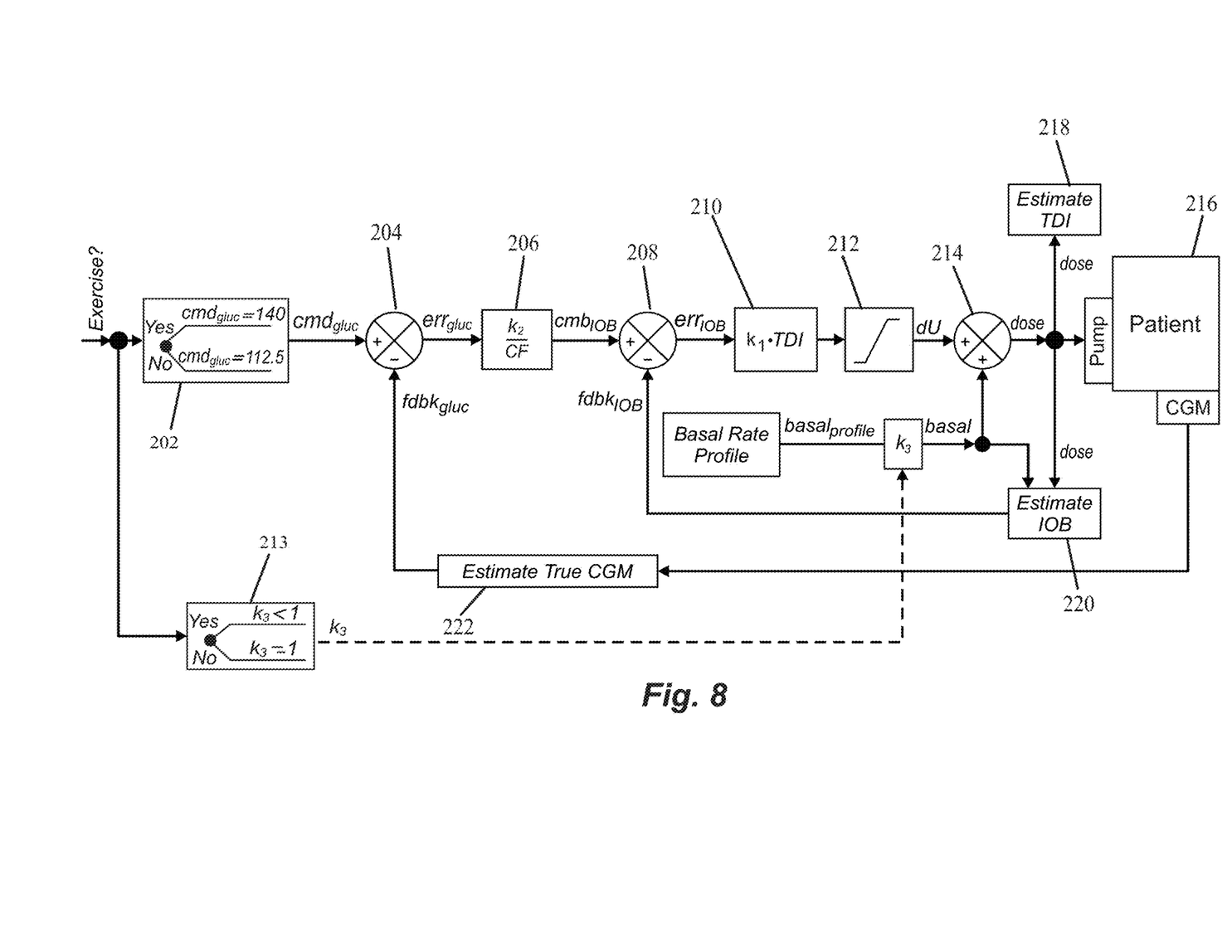
FIG. 8 is a schematic representation of a closed-loop insulin delivery algorithm according to the disclosure.

A third potential modification to the algorithm of FIG. 5 is depicted in FIG. 8 and involves introducing a temporary basal rate and doing so in a manner that does not allow the temporary basal rate to accelerate the burn down or reduction in IOB. Referring to FIG. 8, this is done by determining a constant $k_3$ at step 213 in the control algorithm before conducting the initial glucose level comparison as in FIG. 5. If the user is exercising, the constant is set to less than one and inserted into the algorithm to temporarily reduce the user's stored basal profile used in calculating the estimated IOB at step 220 and the insulin dose for the cycle at step 214. This embodiment therefore results in a reduced dose because the stored basal profile used in the dose calculation at step 214 is reduced, whereas in the previous embodiments the dU in the dose calculation was reduced as a result of a reduced errIOB value. By inserting the temporary basal rate constant at the depicted location in the algorithm, the IOB is computed based on the deviation from the reduced basal rate profile, and therefore does not accelerate the burn down of IOB because both the dose calculated at step 214 and the IOB estimate at step 220 utilize the temporary rate. In contrast, if the temporary rate was introduced after the dose was calculated, it would alter the IOB estimate. As with previous embodiments, the initial glucose set point may or may not be adjusted for exercise at step 202.

Figure 9:
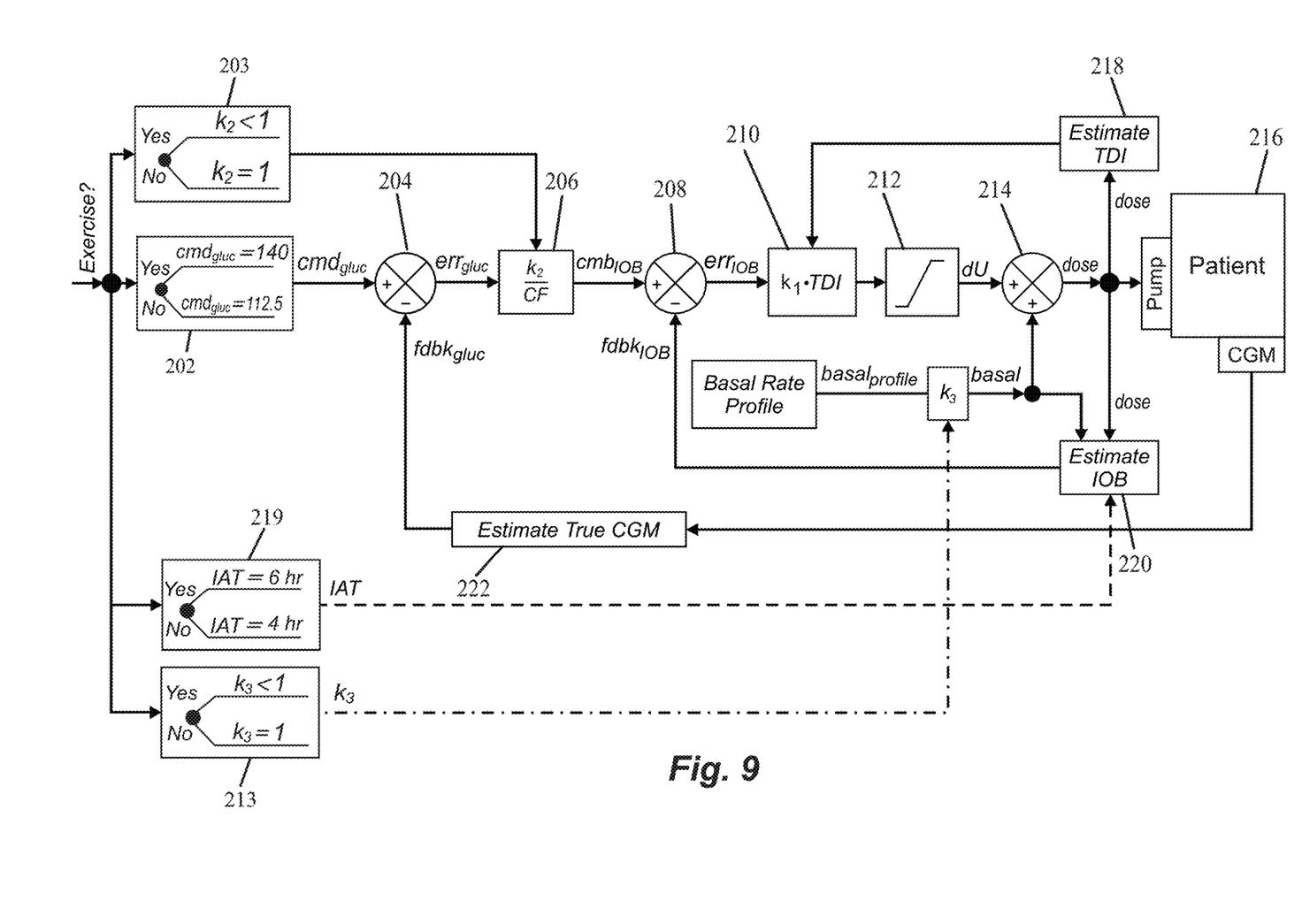
FIG. 9 is a schematic representation of a closed-loop insulin delivery algorithm according to the disclosure.

Each of these three proposed modifications to the basal increase control algorithm of FIG. 5 could be employed individually or in any combination to better account for exercise in closed loop or semi-closed loop diabetes therapy. FIG. 9 depicts an embodiment in which the control algorithm includes all three modifications of FIGS. 6-8. Similar to the above, the initial glucose set point may or may not be adjusted at step 202.

In addition, in some embodiments the number of modifications employed could also be a key aspect of accounting for exercise based on the intensity of the exercise. For example, in setting standard pre-sets for handling exercise, there can be multiple combinations of values such that for light workouts, for example, only one of the options is used, while for heavy workouts, for example, all options are used and may be used with more extreme constant values.

TABLE 1

Potential Exercise Schemes

| Exercise Intensity | IOB Setpoint Reduction (FIG. 6) | Lengthening Insulin Duration Time (FIG. 7) | Temporary Rate (FIG. 8) |
|---|---|---|---|
| Mild | N/A (K2 = 1) | 6 Hours | N/A (K3 = 1) |
| Moderate | K2 = 75% | 6 Hours | N/A (K3 = 1) |
| 60 Minute workout at the gym | K2 = 55% | 6 Hours | K3 = 80% |
| 5K Race | K2 = 40% | 6 Hours | K3 = 20% |
| Marathon | K2 = 20% | 6 Hours | K3 = 0 |

As depicted above, different settings can be prescribed for different levels of exercise including mild exercise, moderate exercise and intense exercise. More intense exercise can further be broken down into various levels including, for example, specific exercise activities such as a 60 minute workout, a 5K race and a marathon. In this embodiment, for mild exercise the algorithm is adjusted only to include the lengthening insulin duration time aspect of the disclosure whereas for moderate exercise both the IOB set-point reduction and lengthening insulin duration time aspects are incorporated. For the more intense types of exercise, all three aspects can be incorporated, with the $k_2$ and $k_3$ constants decreasing as the exercise intensity increases. It should be noted that Table 1 depicts one exemplary embodiment and that which and how many adjustments are applied to a given type and/or intensity of exercise can vary.

Although embodiments described herein may be discussed in the context of the controlled delivery of insulin, delivery of other medicaments, singly or in combination with one another or with insulin, including, for example, glucagon, pramlintide, etc., as well as other applications are also contemplated. Device and method embodiments discussed herein may be used for pain medication, chemotherapy, iron chelation, immunoglobulin treatment, dextrose or saline IV delivery, treatment of various conditions including, e.g., pulmonary hypertension, or any other suitable indication or application. Non-medical applications are also contemplated.

Also incorporated herein by reference in their entirety are commonly owned U.S. Pat. Nos. 6,999,854; 8,133,197; 8,287,495; 8,408,421 8,448,824; 8,573,027; 8,650,937; 8,986,523; 9,173,998; 9,180,242; 9,180,243; 9,238,100; 9,242,043; 9,335,910; 9,381,271; 9,421,329; 9,486,171; 9,486,571; 9,492,608; 9,503,526; 9,555,186; 9,565,718; 9,603,995; 9,669,160; 9,715,327; 9,737,656; 9,750,871; 9,867,937; 9,867,953; 9,940,441; 9,993,595; 10,016,561; 10,201,656; 10,279,105; 10,279,106; 10,279,107; 10,357,603; 10,357,606; 10,492,141; 10/541,987; and 10,569,016. commonly owned U.S. Patent Publication Nos. 2009/0287180; 2012/0123230; 2013/0053816; 2014/0276423; 2014/0276569; 2014/0276570; 2018/0021514; 2018/0071454; 2019/0240398; 2019/0307952; 2019/0365997 and 2020/0114076 and commonly owned U.S. patent application Ser. Nos. 16/507,146; 16/725,278; 16/725,337; 16/793,662 and 16/830,415.

With regard to the above detailed description, like reference numerals used therein may refer to like elements that may have the same or similar dimensions, materials, and configurations. While particular forms of embodiments have been illustrated and described, it will be apparent that various modifications can be made without departing from the spirit and scope of the embodiments herein. Accordingly, it is not intended that the invention be limited by the forgoing detailed description.

The entirety of each patent, patent application, publication, and document referenced herein is hereby incorporated by reference. Citation of the above patents, patent applications, publications and documents is not an admission that any of the foregoing is pertinent prior art, nor does it constitute any admission as to the contents or date of these documents.

Modifications may be made to the foregoing embodiments without departing from the basic aspects of the technology. Although the technology may have been described in substantial detail with reference to one or more specific embodiments, changes may be made to the embodiments specifically disclosed in this application, yet these modifications and improvements are within the scope and spirit of the technology. The technology illustratively described herein may suitably be practiced in the absence of any element(s) not specifically disclosed herein. The terms and expressions which have been employed are used as terms of description and not of limitation and use of such terms and expressions do not exclude any equivalents of the features shown and described or portions thereof and various modifications are possible within the scope of the technology claimed. Although the present technology has been specifically disclosed by representative embodiments and optional features, modification and variation of the concepts herein disclosed may be made, and such modifications and variations may be considered within the scope of this technology.

The invention claimed is:

1. A system for closed loop diabetes therapy, comprising:
   a pump mechanism configured to facilitate delivery of insulin to a user;
   a user interface;
   a communications module adapted to receive glucose levels from a continuous glucose monitor;
   a processor functionally linked to the pump mechanism, the user interface and the communications module, the processor configured to:
   calculate and deliver insulin doses to the user based on a closed loop insulin delivery algorithm, the closed loop insulin delivery algorithm including an outer glucose loop that compares the glucose levels from the continuous glucose monitor to a glucose target to determine an insulin on board target for the user and an inner insulin on board loop that compares an estimated insulin on board for the user to the insulin on board target to determine an insulin on board error used to calculate the insulin doses configured to maintain an insulin on board of the user at the insulin on board target and the glucose levels of the user at the glucose target;
   receive an indication that the user will be exercising;
   activate an exercise mode for the closed loop insulin delivery algorithm in response to the indication that the user will be exercising, the exercise mode modifying the inner insulin on board loop of the closed loop insulin delivery algorithm that calculates the insulin doses to maintain the insulin on board of the user at the insulin on board target; and
   calculate and deliver the insulin doses to the user based on the glucose levels from the continuous glucose monitor according to the exercise mode of the closed loop insulin delivery algorithm following the indication that the user will be exercising.

2. The system of claim 1, wherein the exercise mode modifies the inner insulin on board loop of the closed loop insulin delivery algorithm by modifying the insulin on board error of the inner insulin on board loop.

3. The system of claim 2, wherein the insulin on board error is modified by applying a temporary constant to the insulin on board target to reduce the insulin on board target.

4. The system of claim 2, wherein the exercise mode modifies the insulin on board error of the closed loop insulin delivery algorithm by increasing an insulin action time used in calculating the estimated insulin on board for the user used to determine the insulin on board error.

5. The system of claim 1, wherein the exercise mode modifies the inner insulin on board loop of the closed loop insulin delivery algorithm by modifying a stored basal rate for the user used in calculating the insulin doses to maintain the insulin on board target for the user.

6. The system of claim 1, wherein the indication that the user will be exercising is received through the user interface.

7. The system of claim 1, wherein the processor is configured to calculate and deliver the insulin doses to the user based on the glucose levels from the continuous glucose monitor according to the exercise mode of the closed loop insulin delivery algorithm for a predetermined time following the indication that the user will be exercising.

8. The system of claim 7, wherein the predetermined time is received through the user interface.

9. The system of claim 1, wherein the pump mechanism, the user interface and the processor are part of an ambulatory infusion pump.

10. The system of claim 1, wherein the user interface and the processor are part of a remote control device for remotely controlling an ambulatory infusion pump including the pump mechanism.

11. A method of closed loop diabetes therapy, comprising:
    receiving glucose levels of a user from a continuous glucose monitor;
    calculating insulin doses for the user based on a closed loop insulin delivery algorithm, the closed loop insulin delivery algorithm including an outer glucose loop that compares the glucose levels of the user from the continuous glucose monitor to a glucose level target to determine an insulin on board target for the user and an inner insulin on board loop that compares an estimated insulin on board for the user to the insulin on board target to determine an insulin on board error used to calculate the insulin doses configured to maintain the estimated insulin on board of the user at the insulin on board target and the glucose levels of the user at the glucose level target;
    delivering the calculated insulin doses to the user with a pump mechanism;
    receiving an indication that the user will be exercising;
    activating an exercise mode for the closed loop insulin delivery algorithm in response to the indication that the user will be exercising, the exercise mode modifying the inner insulin on board loop of the closed loop insulin delivery algorithm that calculates the insulin doses to maintain the estimated insulin on board of the user at the insulin on board target; and
    calculating and delivering the insulin doses to the user based on the glucose levels from the continuous glucose monitor according to the exercise mode of the closed loop insulin delivery algorithm following the indication that the user will be exercising.

12. The method of claim 11, wherein the exercise mode modifies the inner insulin on board loop of the closed loop insulin delivery algorithm by modifying the insulin on board error of the inner insulin on board loop.

13. The method of claim 12, wherein the insulin on board error is modified by applying a temporary constant to the insulin on board target to reduce the insulin on board target.

14. The method of claim 12, wherein the exercise mode modifies the insulin on board error of the closed loop insulin delivery algorithm by increasing an insulin action time used in calculating the estimated insulin on board for the user used to determine the insulin on board error.

15. The method of claim 11, wherein the exercise mode modifies the inner insulin on board loop of the closed loop insulin delivery algorithm by modifying a stored basal rate for the user used in calculating the insulin doses to maintain the insulin on board target for the user.

16. The method of claim 11, further comprising receiving the indication that the user will be exercising through a user interface.

17. The method of claim 11, wherein the insulin doses are calculated and delivered to the user based on the glucose levels from the continuous glucose monitor according to the exercise mode for a predetermined time following the indication that the user will be exercising.

18. The method of claim 17, further comprising receiving the predetermined time through a user interface.

19. The method of claim 11, wherein the pump mechanism is part of an ambulatory infusion pump that calculates the insulin doses.

\* \* \* \* \*